US012622733B2

(12) United States Patent
    Burki et al.

(10) Patent No.: US 12,622,733 B2
(45) Date of Patent: May 12, 2026

(54) OLECRANON BONE PLATE

(71) Applicant: Bonebridge AG, Zug (CH)

(72) Inventors: Patrick Burki, Solothurn (CH); Beat Kaspar Moor, Venthône (CH); Christian Spross, Staad (CH); Martin Olach, St. Gallen (AT)

(73) Assignee: Bonebridge AG, Zug (CH)

( * ) Notice: Subject to any disclaimer, the term of this patent is extended or adjusted under 35 U.S.C. 154(b) by 110 days.

(21) Appl. No.: 18/580,100

(22) PCT Filed: Aug. 10, 2021

(86) PCT No.: PCT/CH2021/050016
    § 371 (c)(1),
    (2) Date: Jan. 17, 2024

(87) PCT Pub. No.: WO2023/015400
    PCT Pub. Date: Feb. 16, 2023

(65) Prior Publication Data
    US 2024/0315744 A1     Sep. 26, 2024

(51) Int. Cl.
    A61B 17/80          (2006.01)

(52) U.S. Cl.
    CPC ...... A61B 17/8057 (2013.01); A61B 17/8061 (2013.01)

(58) Field of Classification Search
    CPC .................... A61B 17/8057; A61B 17/8061
    See application file for complete search history.

(56) References Cited

U.S. PATENT DOCUMENTS 8,182,517  B2    5/2012  Sixto, Jr. et al.
2004/0116930  A1    6/2004  O'Driscoll 2009/0118770  A1*   5/2009  Sixto, Jr. ............ A61B 17/8061
                                                        606/301
2015/0196333  A1    7/2015  Austin et al.
2021/0106368  A1    4/2021  Zingalis et al.

FOREIGN PATENT DOCUMENTS

EP          3808295  A1     4/2021
FR          2899094  A1    10/2007

OTHER PUBLICATIONS

International Search Report dated May 27, 2022 filed in PCT/CH2021/050016.

* cited by examiner

*Primary Examiner* — Olivia C Chang
(74) *Attorney, Agent, or Firm* — Rankin, Hill & Clark LLP

(57)            ABSTRACT

The bone plate (1) according to the invention is particularly suitable for treating fractures or non-unions and for osteotomies of the olecranon and the proximal ulna. The bone plate (1) has the following parts:

a distal longitudinal shaft portion (2) having a number of plate holes (11);

a longitudinal central axis (3); and a proximal head part (4), which is widened compared to the distal shaft part and has two holes (5; 6) with the hole axes (7, 8) arranged on opposite sides of the central axis (3), wherein the head part (4) is bent down relative to the shaft part (2).

The two holes (5, 6) are suitable for receiving a polyaxial locking screw at an angle of ±15° relative to the respective hole axis (7; 8) or a non-locking standard screw, with the two hole axes (7, 8) forming an angle α.

19 Claims, 2 Drawing Sheets

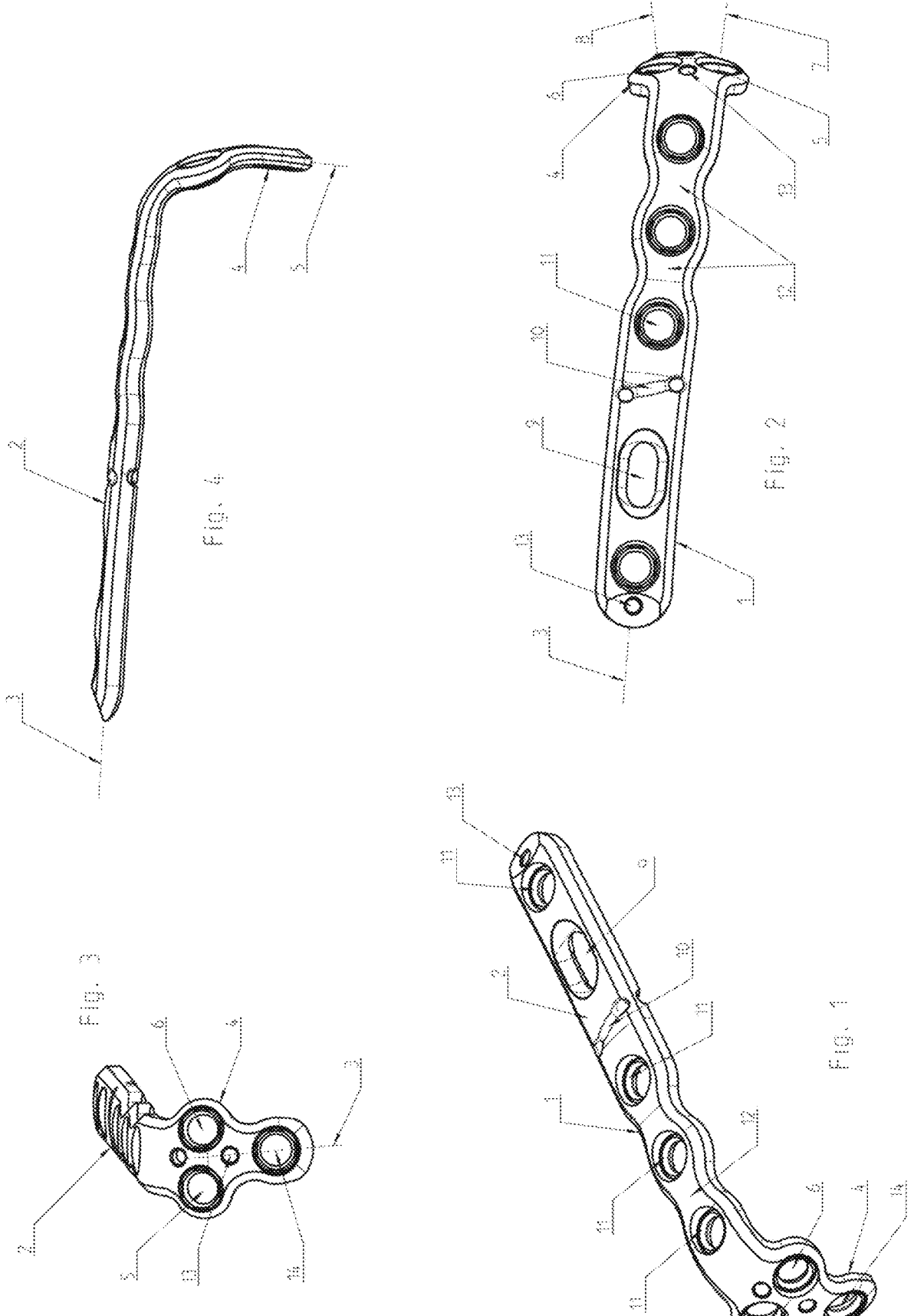

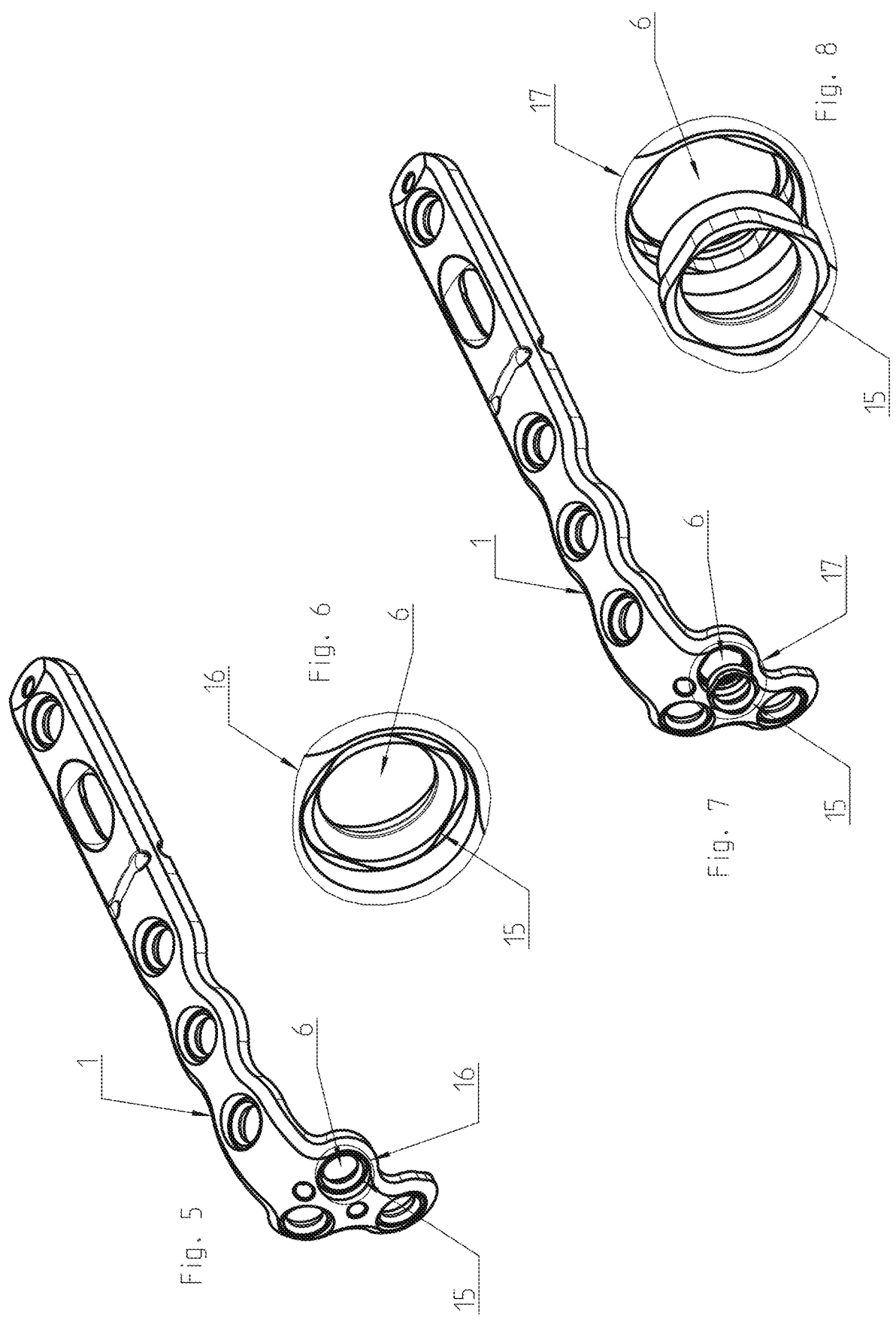

OLECRANON BONE PLATE

BACKGROUND OF INVENTION

Field of Invention

The invention relates to a bone plate suitable for the treatment of fractures or non-unions and for osteotomies of the olecranon and the proximal ulna.

Brief Description of Related Art

Proximal ulna/olecranon fractures are relatively common injuries in adults and can result in severe dysfunction resulting from post-traumatic instability, impingement, soft tissue contractures, malunion, or nonunion. High-energy injuries can lead to associated distal injuries such as: forearm and distal radius fractures, fractures including the intraosseous membrane or disruptions of the distal radioulnar joint. Monteggia fractures are fractures of the proximal third of the ulna with associated radial head dislocation.

The bone plate according to the invention is intended for use in open reduction and internal fixation (ORIF) of the olecranon and the proximal ulna. It is indicated for fractures, osteotomies and non-unions of the olecranon and proximal ulna.

From U.S. Pat. No. 8,182,517 a bone plate is known for the internal fixation of a fracture of the proximal ulna, which has a narrow, proximal head part which is bent down relative to the wider, distal shaft part and one or two hole(s) arranged on the longitudinal central axis of the bone plate.

However, this known bone plate has the disadvantage that the bent-down head part is short and narrow relative to the shaft part, so that not all intra-articular fractures can be treated with it. In addition, it is difficult to properly fix the fragments resulting from a fracture with just one screw (or two longitudinally arranged screws).

The invention aims to provide a remedy here. The invention is based on the object of creating a bone plate for the olecranon, which allows any type of fracture to be treated.

BRIEF SUMMARY OF THE INVENTION

The invention solves the problem with a bone plate with (i) a distal longitudinal shaft portion having a number of plate holds, (ii) a longitudinal central axis, and (iii) a proximal head part, which is widened compared to the distal shaft part and has two holes with the hole axes arranged an opposite sides of the central axis, wherein a) the head part is bent down relative to the shaft part; b) the two holes are suitable for receiving (i) a polyaxial locking screw at an angle of ±15° relative to the respective hole axis or (ii) a non-locking standard screw; and c) the two hole axes from an angle a; a combination of a bone plate according to the invention with at least one polyaxial bone screw; and use of the bone plate according to the invention for the treatment of fractures or non-unions and for osteotomies of the olecranon and the proximal ulna.

The advantages achieved by the invention can essentially be seen in the fact that, thanks to the bone plate according to the invention with a widened head part, which is equipped with three screw holes, a broken olecranon can be optimally supported. By means of the two screw holes located to the left and right of the central axis, two screws can be placed almost parallel to the shaft part, so that all intermediate fragments can be optimally gripped and optimal mechanical stability is achieved.

Further advantageous embodiments of the invention can be commented on as follows:

In a special embodiment of the bone plate according to the invention, the proximal head part has a third hole with a hole axis which is arranged centrally to the central axis. Thanks to the additional third hole, practically all possible fractures can be treated with the bone plate. For example, this third, most proximally located hole can also be used to treat a simple intra-articular olecranon fracture. Rarely are all three proximal holes equipped with bone screws, because if they were, the space would be too tight, but depending on the fracture, the surgeon has the choice of where he would like to place a screw in the head part.

The length $L_K$ of the proximal head part bent down relative to the shaft part is at least 20%, preferably at least 25% of the length $L_S$ of the shaft part. The relatively long head part makes it possible to support the entire proximal olecranon.

In a further embodiment, the free proximal end of the head part is bent down by at least 70°, preferably at least 80°, relative to the distal shaft part.

In a special embodiment, the two hole axes converge distally and the angle $\alpha$ is greater than 1°, preferably greater than 4°. This ensures that the polyaxial screws cannot be shot into the joint when they are set in the zero degree direction to the hole axis.

In a further embodiment, the centers of all plate holes in the distal shaft part are at most 2 mm away from the central axis.

In a special embodiment, at least one of the holes or the plate holes has an inner wall made of a material that has a hardness $H_P$. In addition, a hollow cylindrical or hollow cone-shaped insert is mounted in the plate hole, which rests at least partially on the inner wall and is suitable for receiving the head of a bone screw, the insert being arranged in the plate hole so that it cannot rotate and being made of a material that has a hardness $H_E < H_P$. This makes it possible to place a locking screw in the circular plate holes.

In a further embodiment, the distal shaft part has an elongated hole for exerting axial or interfragmentary compression.

In a special embodiment, the distal shaft part has a thread hole with a smaller diameter compared to the diameter of the holes, which is suitable for fixing surrounding soft tissues to the bone plate. The thread hole is expediently arranged between the elongated hole and the plate hole closest to the proximal end.

In a particular embodiment, the average thickness of the bone plate in the transition zone between the distal shaft part and the proximal head part is smaller than the average thickness of the distal shaft part, preferably 10% smaller.

In a further embodiment, a constriction is provided at least between two plate holes of the distal shaft part, so that the width is preferably reduced by at least 20%, which makes it easier for the surgeon to bend the bone plate. The area moment of inertia of the plate cross section at the narrowest point of the constriction advantageously corresponds essentially to the area moment of inertia of the plate cross section in the area of the largest diameter of the adjacent plate hole. This means that the bone plate can be bent equally well everywhere and there are no weak points under constant stress.

In a further embodiment of the bone plate according to the invention, the proximal head part has a through hole for receiving a Kirschner wire, the hole axis of which preferably runs parallel to one of the hole axes of the holes. This allows the fracture to be reduced and held in place and the optimal screw alignment to be defined.

Advantageously, the distal shaft part is free of lateral wings that run transversely to the central axis, in particular those with a screw hole.

In a special embodiment of the bone plate according to the invention, the length $L_K$ of the proximal bent-down head part relative to the shaft part is in the range of 16-24 mm, preferably in the range of 17-23 mm.

The bone plate according to the invention can also be designed in a mirror image.

The bone plate according to the invention can be provided both as such and in combination with at least one polyaxial bone screw, for example in the form of a sterile kit.

The bone plate according to the invention is particularly suitable for treating fractures or non-unions and for osteotomies of the olecranon and the proximal ulna.

BRIEF DESCRIPTION OF THE DRAWINGS

The invention and further developments of the invention are explained in more detail below using the partially schematic representations of an exemplary embodiment.

In the drawings:

FIG. 1 is a side perspective view of an embodiment of the bone plate according to the invention;

FIG. 2 is a front perspective view of the embodiment shown in FIG. 1;

FIG. 3 is a further perspective view from above of the embodiment shown in FIG. 1;

FIG. 4 is a side view of the embodiment shown in FIG. 1;

FIG. 5 is a side perspective view of an embodiment of a bone plate according to the invention that includes an insert arranged in a plate hole;

FIG. 6 is an enlargement of an area of FIG. 6;

FIG. 7 is an exploded view of the bone plate shown in FIG. 5 showing the insert before it has been arranged in the plate hole; and FIG. 8 is an enlargement of an area of FIG. 7.

DETAILED DESCRIPTION OF THE INVENTION

The embodiment shown in FIGS. 1 to 4 shows a bone plate 1 for treating fractures or non-unions and for osteotomies of the olecranon and the proximal ulna.

As shown in FIG. 1, the bone plate 1 consists of a distal longitudinal shaft part 2 and an adjoining proximal head part 4. The length of the proximal head part 4, which is bent down relative to the shaft part 2, is approximately 20 mm, which corresponds to approximately 30% of the length of the shaft part 2.

The distal shaft part 2 has four plate holes 11 arranged along the central axis 3 and one elongated hole 9. The bone plate 1 has a longitudinal central axis 3.

The centers of all plate holes 11 and the elongated hole 9 in the distal shaft part 2 are located on the central axis 3. The distal shaft part 2 also has a thread hole 10 for receiving a thread with which surrounding soft tissues can be fixed to the bone plate 1.

The thread hole 10 is expediently arranged between the elongated hole 9 and the plate hole 11 closest to the proximal end. The elongated hole 9 lies between the three plate holes arranged proximally and the fourth plate hole 11 arranged distally therefrom. The most distal region of the shaft part 2 is beveled and has a through hole 13 for receiving a Kirschner wire.

Between each pair of plate holes 11 of the distal shaft part 2, which has a width of 10.4 mm, there is a constriction 12 which reduces the shaft width in this area to 7.5 mm.

The head part 4 is bent down relative to the distal shaft part 2. From FIG. 4 it can be seen that the most proximal region of the head part 4 has an angle of approximately 90° to the shaft part 2. The head part 4 is also widened compared to the shaft part 2.

The thickness of the bone plate 1 in the transition zone between the distal shaft part 2 and the proximal head part 4 is smaller than the average thickness of the distal shaft part 2 of 3.2 mm and varies between 2.5-2.8 mm.

The proximal head part 4 has a total of three holes 5, 6 and 14, two of the three holes 5, 6 being arranged on opposite sides of the central axis 3 and the third hole 14 being arranged on the central axis 3. The holes 5, 6 located on opposite sides of the central axis 3 have hole axes 7, 8 which converge distally, forming an angle α of 7°. The two holes 5, 6 are designed in such a way that they are suitable for receiving both (i) polyaxial locking screws at an angle of ±15° relative to their respective hole axes 7; 8 and (ii) non-locking standard screws.

The head part 4 also has two through holes 13 for receiving a Kirschner wire; one through hole 13 is arranged distally to the centrally arranged third hole 14 and the second through hole 13 lies distally between the two holes 5, 6 arranged to the right and left of the central axis 3.

As a variant of the embodiment according to FIGS. 1-4, the distal shaft part 2 can have eight plate holes 11 instead of four, three of them being arranged proximal to the elongated hole 9 and the remaining five distal to the elongated hole 9. In this bone plate with an extended shaft part 2, the length of the proximal head part 4, which is bent down relative to the shaft part 2, is approximately 15% of the length of the shaft part 2.

With reference to FIGS. 5-8, in a special embodiment at least one of the holes 5, 6 or the plate holes 11 of the bone plate 1 has an inner wall made of a material that has a hardness HP. In addition, a hollow cylindrical or hollow cone-shaped insert 15 is mounted in the at least one of the holes 5, 6 or the plate holes 11. which rests at least partially on the inner wall and is suitable for receiving the head of a bone screw, the insert being arranged in the plate hole so that it cannot rotate and being made of a material that has a hardness HE <HP. This makes it possible to place a locking screw in the circular plate holes. FIG. 5 is a side perspective view of an embodiment of a bone plate 1 that includes an insert 15 arranged in a plate hole 6. FIG. 6 is an enlargement of an area 16 of FIG. 6. FIG. 7 is an exploded view of the bone plate 1 shown in FIG. 5 showing the insert 15 before it has been arranged in the plate hole 6. And, FIG. 8 is an enlargement of an area 17 of FIG. 7.

While there are various embodiments of the present invention as described above, it is to be understood that the various features may be used individually or in any combination.

This invention is therefore not simply limited to the particularly preferred embodiments mentioned above.

The invention claimed is:

1. A bone plate comprising:
   a distal longitudinal shaft part provided with a plurality of shaft part plate holes; and
   a proximal head part, which is wider than the distal longitudinal shaft part and which is provided with first and second head part holes;
   wherein the bone plate has a central axis, wherein the first and second head part holes have hole axes arranged on opposite sides of the central axis, wherein the proximal head part is angled relative to the distal longitudinal shaft part, wherein the first and second head part holes are configured to receive (i) a polyaxial locking screw at an angle of ±15° relative to the respective hole axis, or (ii) a non-locking standard screw, and wherein the hole axes of the first and second head part holes converge distally at an angle α that is greater than 1°.

2. The bone plate according to claim 1, wherein the proximal head part is provided with a third hole having a hole axis, which is arranged on the central axis.

3. The bone plate according to claim 1, proximal head part angled relative to the distal longitudinal shaft part has a length $L_K$ that is at least 20% a length $L_S$ of the distal longitudinal shaft part.

4. The bone plate according to claim 1, wherein a free proximal end of the proximal head part is angled by at least 70° relative to the distal longitudinal shaft part.

5. The bone plate according to claim 1, wherein the angle α is greater than 4°.

6. The bone plate according to claim 1, wherein centers of all shaft part plate holes are not more than 2 mm away from the central axis.

7. The bone plate according to claim 1, wherein at least one of the first and second head part holes or the shaft part plate holes has an inner wall made of a material that has a hardness $H_P$ within which is mounted a hollow cylindrical or hollow cone-shaped insert, which rests at least partially on the inner wall and is configured to receive a head of a bone screw, the insert being arranged in the plate hole and secured against rotation and consisting of a material that has a hardness $H_E$, and wherein $H_E < H_P$.

8. The bone plate according to claim 1, wherein the distal longitudinal shaft part is provided with an elongated hole.

9. The bone plate according to claim 8, wherein the distal longitudinal shaft part is provided with a thread hole having a diameter that is smaller than the diameter of the first and second head part holes, which is configured for fixing surrounding soft tissues to the bone plate.

10. The bone plate according to claim 9, wherein the thread hole is arranged between the elongated hole and the next shaft part plate hole in the direction of the proximal head part.

11. The bone plate according to claim 1, wherein the bone plate has an average thickness in a transition zone between the distal longitudinal shaft part and the proximal head part that is smaller than an average thickness of the distal longitudinal shaft part.

12. The bone plate according to claim 1, wherein a constriction is provided at least between two shaft part plate holes such that at the constriction the distal longitudinal shaft part width is reduced by at least 20%.

13. The bone plate according to claim 12, wherein the area moment of inertia of the plate cross section at the narrowest point of the constriction essentially corresponds to the area moment of inertia of the plate cross section in the area of the largest diameter of the adjacent plate hole.

14. The bone plate according to claim 1, wherein the proximal head part is provided with a through hole for receiving a Kirschner wire.

15. The bone plate according to claim 1, wherein the distal longitudinal shaft part does not have lateral wings running transversely to the central axis.

16. The bone plate according to claim 3, wherein the length $L_K$ of the proximal head part angled relative to the distal longitudinal shaft part is in the range of 16-24 mm.

17. The bone plate according to claim 1, wherein the bone plate has a geometrical shape adapted for fixation to a right ulna.

18. The bone plate according to claim 1, wherein the bone plate has a geometrical shape adapted for fixation to a left ulna.

19. A combination comprising a bone plate according to claim 1 and at least one polyaxial bone screw.

* * * * *